(12) United States Patent
Kawamura et al.

(10) Patent No.: US 11,293,427 B2
(45) Date of Patent: Apr. 5, 2022

(54) VALVE, AND FLUID CONTROL DEVICE INCLUDING VALVE

(71) Applicant: Murata Manufacturing Co., Ltd., Kyoto (JP)

(72) Inventors: Kenichiro Kawamura, Kyoto (JP); Yukiharu Kodama, Kyoto (JP); Hiroshi Takemura, Kyoto (JP); Hiroki Achiwa, Kyoto (JP)

(73) Assignee: MURATA MANUFACTURING CO., LTD., Kyoto (JP)

( * ) Notice: Subject to any disclaimer, the term of this patent is extended or adjusted under 35 U.S.C. 154(b) by 0 days.

(21) Appl. No.: 16/944,744

(22) Filed: Jul. 31, 2020

(65) Prior Publication Data

US 2020/0355278 A1 Nov. 12, 2020

Related U.S. Application Data

(63) Continuation of application No. PCT/JP2018/048512, filed on Dec. 28, 2018.

(30) Foreign Application Priority Data

Mar. 9, 2018 (JP) .............................. JP2018-043271

(51) Int. Cl.
*F16K 7/17* (2006.01)
*F04B 43/04* (2006.01)
(Continued)

(52) U.S. Cl.
CPC .......... *F04B 43/046* (2013.01); *A61B 5/0235* (2013.01); *F04B 49/22* (2013.01);
(Continued)

(58) Field of Classification Search
CPC .. F04B 43/046; F04B 53/1062; F04B 45/047; A61B 5/0235; F16K 7/17; F16K 11/022; F16K 99/0015; F16K 27/0236
See application file for complete search history.

(56) References Cited

U.S. PATENT DOCUMENTS 4,826,131 A * 5/1989 Mikkor .............. F02M 61/1853
239/585.3
2013/0178752 A1 7/2013 Kodama et al.
(Continued)

FOREIGN PATENT DOCUMENTS

JP 2009-156454 A 7/2009
JP 2017-026155 A 2/2017
(Continued)

OTHER PUBLICATIONS

International Search Report issued in Application No. PCT/JP2018/048512, dated Feb. 26, 2019.
(Continued)

*Primary Examiner* — Umashankar Venkatesan
(74) *Attorney, Agent, or Firm* — Pearne & Gordon LLP

(57) ABSTRACT

A valve includes a first valve housing, a second valve housing, a diaphragm, a first fixing part, and a second fixing part. The diaphragm defines an upstream valve chamber together with the first valve housing. The diaphragm defines a downstream valve chamber together with the second valve housing. The diaphragm is movable between a first position in which the diaphragm blocks communication between the upstream valve chamber and the downstream valve chamber, and a second position in which the diaphragm allows communication between the upstream valve chamber and the downstream valve chamber. When in its second position, the diaphragm makes contact with the inlet of the second discharge channel or the wall surface of the downstream valve chamber to seal between the second discharge channel and the first discharge channel, and when in its first position, the diaphragm allows communication between the first discharge channel and the second discharge channel.

20 Claims, 5 Drawing Sheets

(51) Int. Cl.
  *A61B 5/0235* (2006.01)
  *F04B 49/22* (2006.01)
  *F16K 27/02* (2006.01)
  *F04B 45/047* (2006.01)

(52) U.S. Cl.
  CPC ............ *F16K 7/17* (2013.01); *F16K 27/0236* (2013.01); *F04B 45/047* (2013.01)

(56) References Cited

U.S. PATENT DOCUMENTS

| | | |
|---|---|---|
| 2016/0076537 A1 | 3/2016 | Kawamura et al. |
| 2017/0215744 A1* | 8/2017 | Kawamura ............ A61B 5/0235 |
| 2017/0222123 A1* | 8/2017 | Chen ................... F16K 99/0015 |
| 2018/0368704 A1 | 12/2018 | Kawamura et al. |
| 2019/0353157 A1* | 11/2019 | Mou ................... F16K 99/0057 |

FOREIGN PATENT DOCUMENTS

| | | |
|---|---|---|
| WO | 2012/141113 A1 | 10/2012 |
| WO | 2016/063710 A1 | 4/2016 |
| WO | 2018/020882 A1 | 2/2018 |
| WO | 2018/021099 A1 | 2/2018 |

OTHER PUBLICATIONS

Written Opinion issued in Application No. PCT/JP2018/048512, dated Feb. 26, 2019.

* cited by examiner

VALVE, AND FLUID CONTROL DEVICE INCLUDING VALVE

This is a continuation of International Application No. PCT/JP2018/048512 filed on Dec. 28, 2018 which claims priority from Japanese Patent Application No. 2018-043271 filed on Mar. 9, 2018. The contents of these applications are incorporated herein by reference in their entireties.

BACKGROUND OF THE DISCLOSURE

Field of the Disclosure

The present disclosure relates to a valve, and a fluid control device including a valve.

Description of the Related Art

In related art, fluid control devices including a valve have been disclosed (see, for example, Patent Document 1).

A fluid control device disclosed in Patent Document 1 is used to measure blood pressure. The fluid control device includes a piezoelectric pump, a valve, and a cuff. The piezoelectric pump sends pressurized fluid to the valve, and the valve switches whether to allow communication between the piezoelectric pump and the cuff. The valve is provided with a diaphragm to switch between communicating and non-communicating states. When the piezoelectric pump is operating, the diaphragm is in its communicating position, and pressurized fluid sent from the piezoelectric pump is sent to the cuff by way of the valve. When the piezoelectric pump stops operation, the supply of pressurized fluid stops, and the diaphragm moves to its non-communicating position. At this time, the interior of the valve is open to the atmospheric pressure, and thus pressurized fluid stored in the cuff returns to the valve and then exhausted to the outside by way of the valve.

The fluid control device disclosed in Patent Document 1 includes a first valve housing and a second valve housing that define the exterior of the valve. The diaphragm is disposed in the internal space defined by the first valve housing and the second valve housing. The diaphragm is fixed at a predetermined location with its outer edge portion sandwiched from above and below by the first valve housing and the second valve housing. The diaphragm is exposed to the outside of the valve at its outer peripheral end.

Patent Document 1: Japanese Unexamined Patent Application Publication No. 2017-26155

BRIEF SUMMARY OF THE DISCLOSURE

In recent years, there is a demand for increasing the reliability of fluid control devices. With the configuration described in Patent Document 1, when the piezoelectric pump is operating, the central portion of the diaphragm is subjected to an elevated pressure due to the pressurized fluid inside the valve, whereas the outer peripheral end of the diaphragm is subjected to atmospheric pressure. A large differential pressure thus develops across the diaphragm. Consequently, as the operation of the piezoelectric pump proceeds, the diaphragm may gradually deteriorate, leading to poor valve operation. This may result in decreased reliability of the valve and the fluid control device including the valve.

Accordingly, an object of the present disclosure is to address the above-mentioned problem by providing a valve and a fluid control device that have improved reliability.

To attain the above-mentioned object, a valve according to the present disclosure includes a first valve housing, a second valve housing, a diaphragm, a first fixing part, and a second fixing part. The first valve housing has an inlet for pressurized fluid, and a valve seat. The second valve housing has a first discharge channel for pressurized fluid, and a second discharge channel for pressurized fluid. The second valve housing is stacked over the first valve housing. The diaphragm is disposed between the first valve housing and the second valve housing, and has a communication opening. The first fixing part fixes the outer edge region of the first valve housing, and the outer edge region of the second valve housing to each other. The second fixing part is disposed inward of the first fixing part in a plan view to fix the diaphragm to one of the first valve housing and the second valve housing. The diaphragm defines an upstream valve chamber together with the first valve housing. The diaphragm defines a downstream valve chamber together with the second valve housing. The diaphragm is movable between a first position and a second position. The first position is a position in which a portion of the diaphragm around the communication opening is positioned in contact with the valve seat of the first valve housing to block communication between the upstream valve chamber and the downstream valve chamber. The second position is a position in which the portion of the diaphragm around the communication hole is positioned away from the valve seat of the first valve housing to allow communication between the upstream valve chamber and the downstream valve chamber. When in the second position, the diaphragm makes contact with the inlet of the second discharge channel or with the wall surface of the downstream valve chamber to seal between the second discharge channel and the first discharge channel. When in the first position, the diaphragm allows communication between the first discharge channel and the second discharge channel.

Further, a fluid control device according to the present disclosure includes the valve, and a pump that sends pressurized fluid to the inlet of the first valve housing of the valve.

The valve and the fluid control device according to the present disclosure allow for improved reliability.

DETAILED DESCRIPTION OF THE DISCLOSURE

Figure 1:
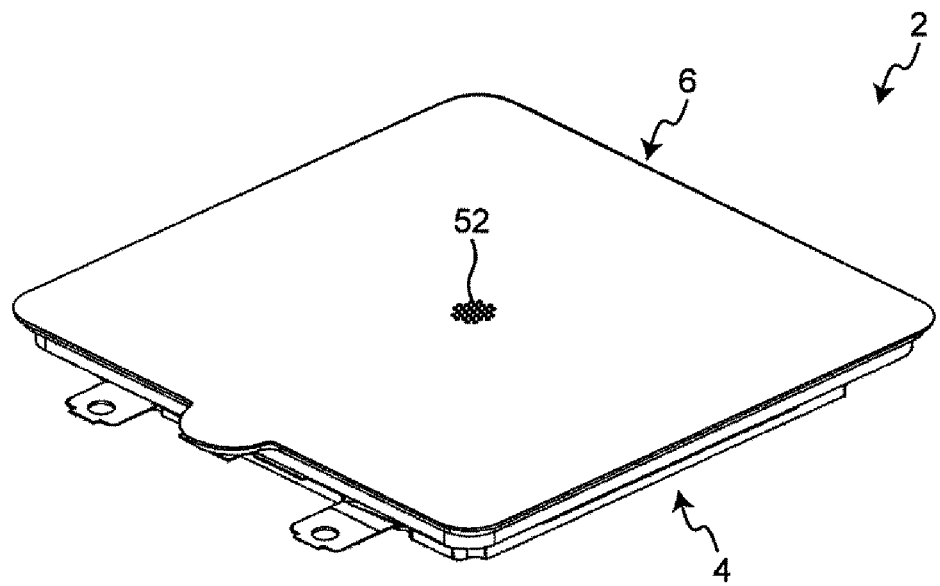
FIG. 1 is a top perspective view of a fluid control device.

A first aspect of the present disclosure provides a valve including a first valve housing, a second valve housing, a diaphragm, a first fixing part, and a second fixing part. The first valve housing has an inlet for pressurized fluid, and a valve seat. The second valve housing has a first discharge channel for pressurized fluid, and a second discharge channel for pressurized fluid. The second valve housing is stacked over the first valve housing. The diaphragm is disposed between the first valve housing and the second valve housing, and has a communication opening. The first fixing part fixes the outer edge region of the first valve housing, and the outer edge region of the second valve housing to each other. The second fixing part is disposed inward of the first fixing part in a plan view to fix the diaphragm to one of the first valve housing and the second valve housing. The diaphragm defines an upstream valve chamber together with the first valve housing. The diaphragm defines a downstream valve chamber together with the second valve housing. The diaphragm is movable between a first position and a second position. The first position is a position in which a portion of the diaphragm around the communication opening is positioned in contact with the valve seat of the first valve housing to block communication between the upstream valve chamber and the downstream valve chamber. The second position is a position in which the portion of the diaphragm around the communication hole is positioned away from the valve seat of the first valve housing to allow communication between the upstream valve chamber and the downstream valve chamber. When in the second position, the diaphragm makes contact with the inlet of the second discharge channel or with the wall surface of the downstream valve chamber to seal between the second discharge channel and the first discharge channel. When in the first position, the diaphragm allows communication between the first discharge channel and the second discharge channel.

With the above-mentioned configuration, the diaphragm is fixed inward of the first fixing part. This configuration ensures that the diaphragm is not exposed to the outside of the valve housings, thus reducing the differential pressure across the surface of the diaphragm in comparison with when the diagram is exposed to the outside of the valve housings. The reduced differential pressure helps to reduce damage to the diaphragm and consequently extend the life of the diaphragm.

A second aspect of the present disclosure provides the valve recited in the first aspect, in which the second fixing part fixes the diaphragm to the second valve housing. As a result, fixing of the diaphragm to the second valve housing is less likely to be obstructed by the valve seat of the first valve housing, thus facilitating manufacture.

A third aspect of the present disclosure provides the valve recited in the first or second aspect, further including a third fixing part disposed between the first fixing part and the second fixing part in a plan view to fix the first valve housing and the second valve housing to each other. With this configuration, the presence of the third fixing part ensures that the first valve housing and the second valve housing can be fixed more firmly in place. This configuration also makes it possible to use a different material for each of the first fixing part, the second fixing part, and the third fixing part.

A fourth aspect of the present disclosure provides the valve recited in the third aspect, in which each of the first fixing part and the second fixing part is a double-faced tape, and the third fixing part is an adhesive. This configuration ensures that the double-faced tape constituting each of the first and second fixing parts is easy to position, and the adhesive constituting the third fixing part has strong adhesion. Further, the adhesive constituting the third fixing part is held back by the first fixing part and the second fixing part, and thus can be placed at a desired location.

A fifth aspect of the present disclosure provides the valve recited in the fourth aspect, in which the third fixing part is a silicone adhesive. This configuration enables use of a general-purpose material to reduce manufacturing cost.

A sixth aspect of the present disclosure provides the valve recited in any one of the third to fifth aspects, in which the first valve housing has a first opposing face and a second opposing face. The first opposing face extends flush from an area where the first valve housing makes contact with the second valve housing in the first fixing part, to a point within an area where the first valve housing makes contact with the second valve housing in the third fixing part. The second opposing face is recessed from the inner edge portion of the first opposing face and extends flush such that the second opposing face is spaced apart from the third fixing part and the diaphragm. With this configuration, a step is provided between the first opposing face and the second opposing face. The presence of the step makes it possible to provide a space for any excess adhesive in the third fixing part to escape.

A seventh aspect of the present disclosure provides the valve recited in any one of the first to sixth aspects, in which when in the second position, the diaphragm makes contact with and blocks the inlet of the second discharge channel to seal between the second discharge channel and the first discharge channel. This configuration ensures that the diaphragm can, when in its second position, seal between the second discharge channel and the first discharge channel with increased precision.

An eighth aspect of the present disclosure provides a fluid control device including the valve recited in any one of the first to seventh aspects, and a pump that sends pressurized fluid to the inlet of the first valve housing of the valve. With the above-mentioned configuration, the diaphragm is fixed inward of the first fixing part. This ensures that the diaphragm is not exposed to the outside of the valve housings, thus reducing the differential pressure across the surface of the diaphragm in comparison with when the diagram is exposed to the outside of the valve housings. The reduced differential pressure helps to reduce damage to the diaphragm and consequently extend the life of the diaphragm.

Embodiment

An embodiment of the present disclosure will be described below in detail with reference to the drawings.
<General Arrangement>

Figure 2:
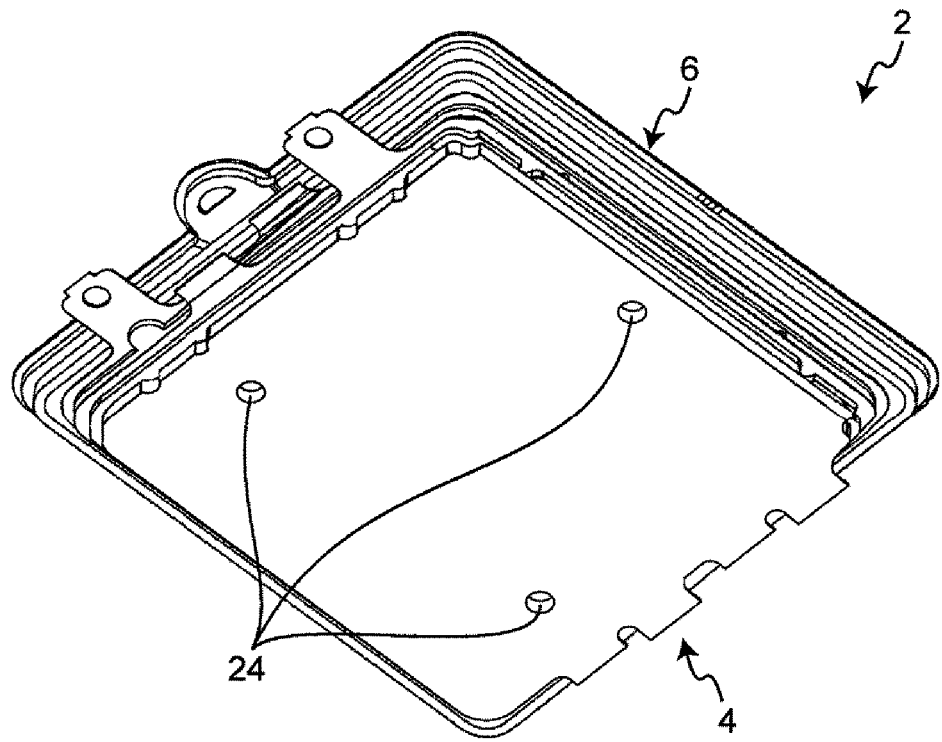
FIG. 2 is a bottom perspective view of the fluid control device.
Figure 3:
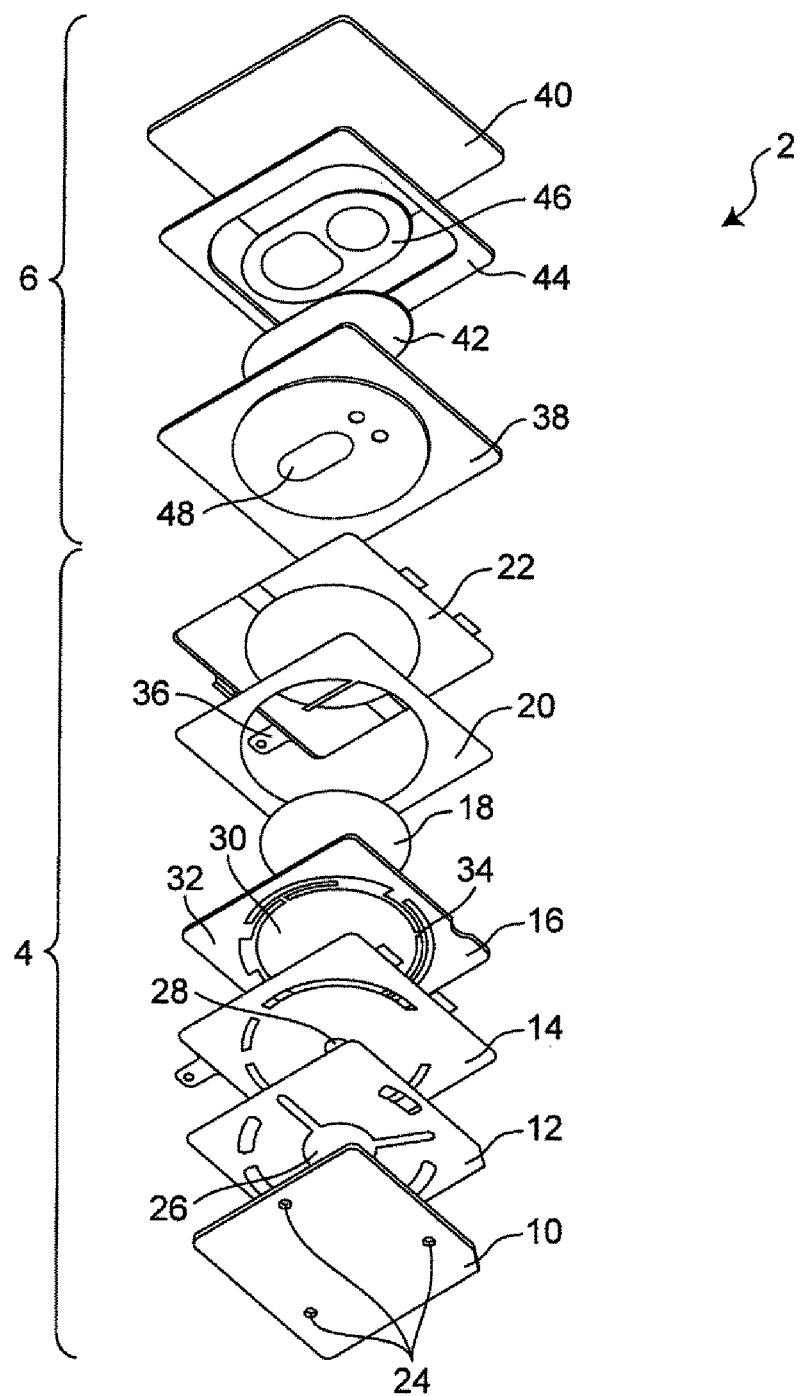
FIG. 3 is an exploded perspective view of the fluid control device.
Figure 4:
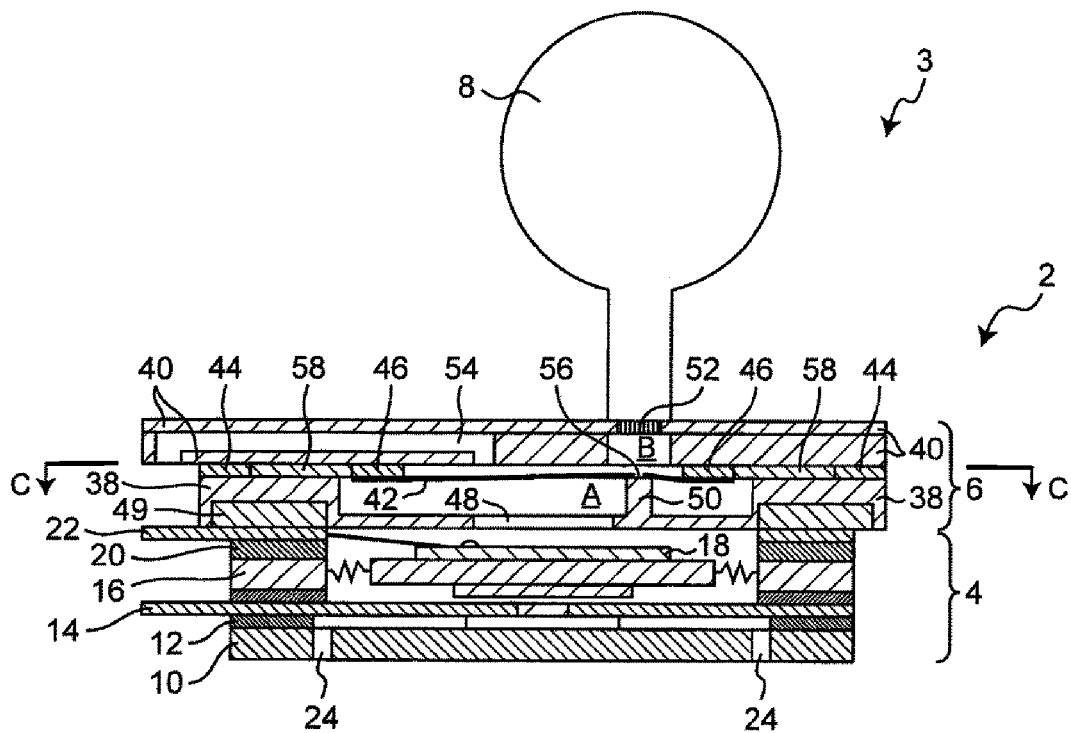
FIG. 4 is a longitudinal sectional view of the fluid control device in a non-operating state prior to its operation.

FIGS. 1 to 4 each illustrate a schematic configuration of a fluid control device 2 according to the embodiment. FIG. 1 is a top perspective view of the fluid control device 2, and FIG. 2 is a bottom perspective view of the fluid control device 2. FIG. 3 is an exploded perspective view of the fluid control device 2, and FIG. 4 is a longitudinal sectional view of the fluid control device 2. FIG. 4 illustrates a non-operating state in which the fluid control device 2 is not operating.

The fluid control device 2 is a device that sucks in fluid (air in the embodiment) through suction openings 24 (FIG. 2), pressurizes the sucked fluid to generate pressurized fluid, and blows out the generated pressurized fluid through a first discharge channel 52 (FIG. 1) in a controlled fashion. As illustrated in FIGS. 1 to 3, the fluid control device 2 includes a pump 4, and a valve 6.

As illustrated in FIG. 4, the fluid control device 2 according to the embodiment is used in a sphygmomanometer 3 that measures human blood pressure. The sphygmomanometer 3 includes a cuff 8 in addition to the fluid control device 2. As the cuff 8 receives supply of pressurized fluid from the fluid control device 2, the cuff 8 inflates and thus functions as an air bag for measuring blood pressure.

The pump 4 sucks in fluid through the suction openings 24 illustrated in FIG. 2 to generate pressurized fluid, and sends the pressurized fluid to the valve 6. The valve 6 can be switched between two modes of operation. In one mode, the valve sends pressurized fluid received from the pump 4 to the cuff 8 through the discharge channel 52. In the other mode, rather than supplying pressurized fluid to the cuff 8, the valve 6 allows pressurized fluid stored in the cuff 8 to be exhausted.

The configuration of the pump 4 and the configuration of the valve 6 will be described below in detail in this order.

As illustrated in FIG. 3, the pump 4 includes a cover 10, a channel plate 12, a thin top plate 14, a spring plate 16, a piezoelectric body 18, an insulating plate 20, and a power feeding plate 22.

The cover 10 is a component provided with the suction openings 24. The cover 10 is affixed to the channel plate 12. The channel plate 12 is a component provided with a channel 26 that communicates with the suction openings 24. The channel plate 12 is affixed to the thin top plate 14. The thin top plate 14 is a component provided with an opening 28 that communicates with the channel 26. The spring plate 16 is a component with its outer periphery portion attached to the thin top plate 14. The spring plate 16 includes a vibrating part 30, a frame part 32, and a connecting part 34. The connecting part 34 is a component that connects and elastically supports the vibrating part 30 and the frame part 32.

The piezoelectric body 18 is affixed to the vibrating part 30. The piezoelectric body 18 is a component that undergoes flexural vibration in response to applied voltage. Due to the presence of the piezoelectric body 18, the pump 4 functions as a piezoelectric pump.

The insulating plate 20 is a component affixed to the frame part 32 of the spring plate 16. The power feeding plate 22 is a component affixed to the insulating plate 20. The power feeding plate 22 includes a terminal 36. The terminal 36 is electrically connected to the piezoelectric body 18, and capable of applying voltage to the piezoelectric body 18.

With the configuration above, when the pump 4 is put into operation and voltage is applied to the piezoelectric body 18 by means of the terminal 36, the piezoelectric body 18, and the vibrating part 30 of the spring plate 16 undergo flexural vibration (e.g., at about 23 kHz). This increases the pressure in the internal space of the pump 4 illustrated in FIG. 4. Due to the increased pressure, air at atmospheric pressure outside the pump 4 is sucked into the pump 4 through the suction openings 24. The air sucked into the pump 4 is pressurized and turns into pressurized fluid. The pressurized fluid generated in the pump 4 is sent to the valve 6.

As illustrated in FIG. 3, the valve 6 includes a first valve housing 38, a second valve housing 40, a diaphragm 42, a first fixing part 44, and a second fixing part 46.

The first valve housing 38 and the second valve housing 40 are both components that define the exterior of the valve 6. The first valve housing 38 has an inlet 48, and a valve seat 50 (FIG. 4). The first valve housing 38 is bonded to the power feeding plate 22 of the pump 4 with an adhesive 49 (FIG. 4). The second valve housing 40 is a component provided with a first discharge channel 52 and a second discharge channel 54. The first valve housing 38 and the second valve housing 40 are stacked over each other.

In the embodiment, the first valve housing 38 and the second valve housing 40 are both made of metal.

The first valve housing 38 and the second valve housing 40 are fixed to each other by the first fixing part 44 illustrated in FIG. 3 or other figures. The diaphragm 42 is disposed in the internal space defined by the first valve housing 38 and the second valve housing 40.

The diaphragm 42 is a component that divides the internal space defined by the first valve housing 38 and the second valve housing 40 into two spaces (valve chambers). As illustrated in FIG. 4, the diaphragm 42 defines an upstream valve chamber (upstream space) A between the diaphragm 42 and the first valve housing 38, and defines a downstream valve chamber (downstream space) B between the diaphragm 42 and the second valve housing 40.

The diaphragm 42 has a communication opening 56 in its central portion. In the non-operating state illustrated in FIG. 4, a portion of the diaphragm 42 around the communication opening 56 makes contact with the valve seat 50 of the first valve housing 38 to form a seal. At this time, the upstream valve chamber A and the downstream valve chamber B are in the non-communicating state in which the two chambers do not communicate with each other. The diaphragm 42 is capable of moving from the non-communicating position illustrated in FIG. 4 to a communicating position in which the diaphragm 42 allows communication between the upstream valve chamber A and the downstream valve chamber B. A description about the specific operation of the diaphragm 42 will be given later.

The diaphragm 42 according to the embodiment is a rubber sheet.

The first fixing part 44 is a component used to fix the first valve housing 38 and the second valve housing 40 to each other. The first fixing part 44 fixes the outer edge region of the first valve housing 38 and the outer edge region of the second valve housing 40 to each other. The first valve housing 38 and the second valve housing 40 are fixed to each other along the entire periphery of their outer edge portions, thus forming a seal at the connection between the first valve housing 38 and the second valve housing 40.

The second fixing part 46 is a component used to fix the diaphragm 42 in place. The second fixing part 46 according to the embodiment fixes the diaphragm 42 to the second valve housing 40. As illustrated in FIGS. 3 and 4, the second fixing part 46 is disposed inward of the first fixing part 44 to fix the diaphragm 42 to the second valve housing 40. The expression "inward of the first fixing part 44" refers to the position relative to the first fixing part 44 with the valve 6 seen in a plan view, that is, seen in a direction perpendicular to the major face of the valve 6 (i.e., in the stacking direction of the valve 6). The diaphragm 42 is fixed in place by the second fixing part 46 along the entire periphery of its outer edge region. The portion of the diaphragm 42 to be fixed in place may not necessarily be the outer edge region but may be a portion of the diaphragm 42 inside the outer edge region. Any portion of the diaphragm 42 may be fixed in place as long as the diaphragm 42 is fixed in place in an annular form so as to divide the upstream valve chamber A and the downstream valve chamber B from each other.

In the non-operating state illustrated in FIG. 4, the diaphragm 42 is fixed in place such that a portion of the diaphragm 42 around the communication opening 56 makes contact with the valve seat 50 of the first valve housing 38 under applied pressure.

In the embodiment, a tacky double-faced tape is used as the first fixing part 44 and the second fixing part 46. A double-faced tape includes a tackifier applied onto both sides of a sheet-like base material. Unlike an adhesive, which has high fluidity, a double-faced tape has no fluidity (i.e., non-fluidic fixing component). As such, a double-faced tape is easy to position, and also less susceptible to leak paths.

In the embodiment, the valve 6 further includes a third fixing part 58 (FIG. 4). As with the first fixing part 44, the third fixing part 58 is a component used to fix the first valve housing 38 and the second valve housing 40 to each other. The third fixing part 58 is disposed between the first fixing part 44 and the second fixing part 46. The third fixing part 58 is not illustrated in FIG. 3.

In the embodiment, an adhesive is used as the third fixing part 58. Unlike the double-faced tape used as the first fixing part 44 and the second fixing part 46, an adhesive is a coating of liquid raw material that is applied and then allowed to harden. An adhesive has high adhesive strength as compared with a double-faced tape. Therefore, using an adhesive makes it possible to strengthen the fixing of the first valve housing 38 and the second valve housing 40.

Unlike a double-faced tape or other such material, an adhesive has high fluidity (i.e., fluidic fixing component). This makes it difficult to place an adhesive at a desired location. In this regard, the third fixing part 58 according to the embodiment is disposed between the first fixing part 44 and the second fixing part 46, and is thus held back by the first fixing part 44 and the second fixing part 46. This allows the third fixing part 58 to be placed at a desired location.

Among various adhesives, a silicone adhesive, in particular, is used as the third fixing part 58 according to the embodiment. Using such a general-purpose material helps to reduce the manufacturing cost of the fluid control device 2.

As described above, the third fixing part 58 is an adhesive with high fluidity, which is difficult to apply in a controlled fashion and thus tends to be applied unevenly. In the embodiment, an escape hole is provided to allow any excess adhesive to escape. Such an escape hole will be described below in more specific detail with reference to FIGS. 5A and 5B.

Figure 5A:
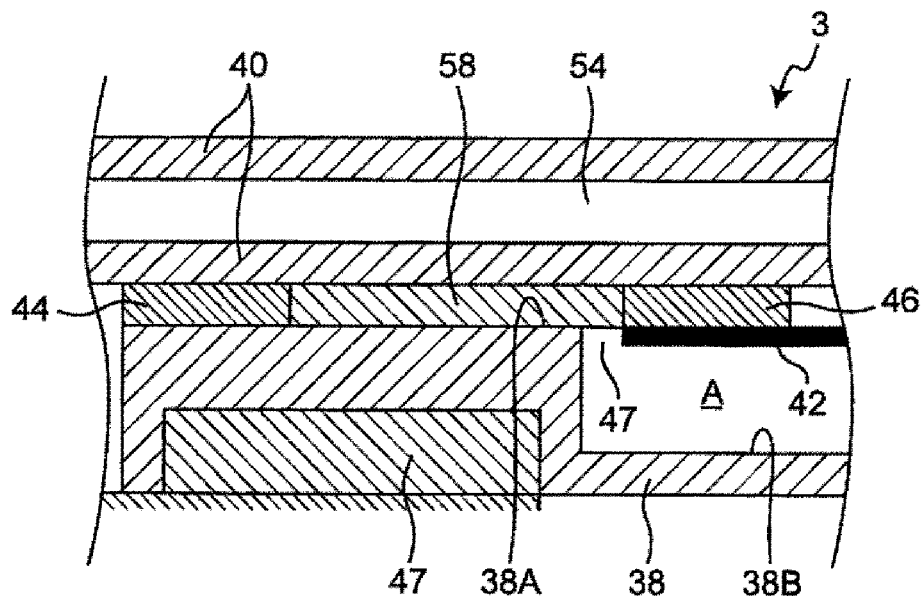
FIG. 5A is a partial enlarged sectional view of a valve.
Figure 5B:
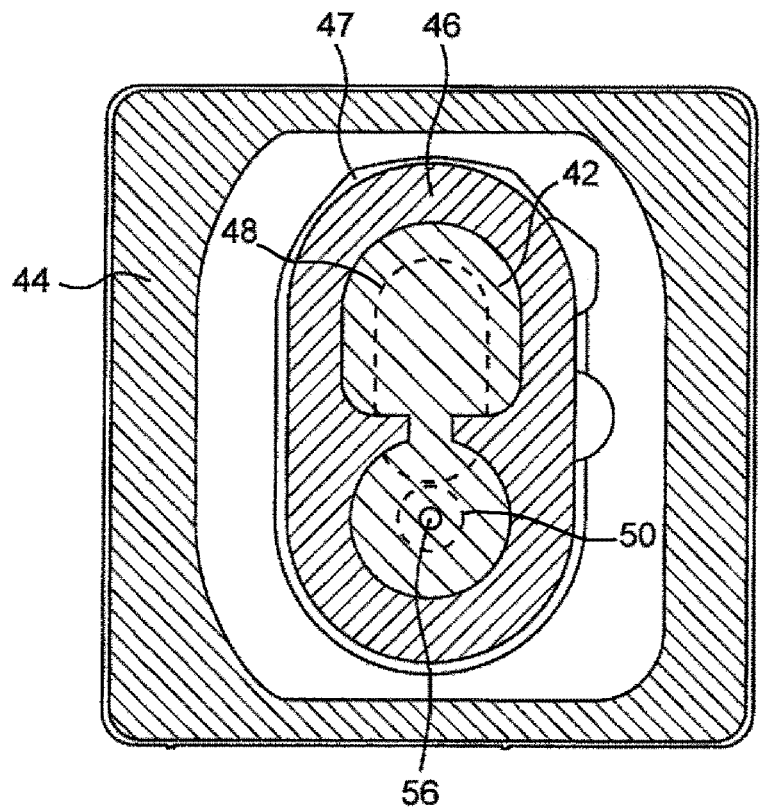
FIG. 5B is a sectional view taken along a line C-C in FIG. 4.

FIG. 5A is a partial enlarged sectional view of the valve 6, and FIG. 5B is a sectional view taken along a line C-C in FIG. 4. As illustrated in FIG. 5A, the first valve housing 38 has a first opposing face 38A and a second opposing face 38B as its faces opposing to the second valve housing 40. The first opposing face 38A extends flush from an area where the first valve housing 38 makes contact with the second valve housing 40 in the first fixing part 44, to a point within an area where the first valve housing 38 makes contact with the second valve housing 40 in the third fixing part 58. The second opposing face 38B is recessed from the inner edge portion of the first opposing face 38A and extends flush such that the second opposing face 38B is spaced apart from the third fixing part 58 and the diaphragm 42.

By providing a step between the first opposing face 38A and the second opposing face 38B as described above, an escape hole 47 can be defined between the diaphragm 42 and the first and second opposing faces 38A and 38B. The third fixing part 58 is exposed to the upstream valve chamber A through the escape hole 47. The presence of the escape hole 47 makes it possible to provide a space for any excess adhesive in the third fixing part 58 to escape. This helps to improve the precision of the fixing performed by using the third fixing part 58. The third fixing part 58 is not illustrated in FIG. 5B.

As illustrated in FIG. 5B, the escape hole 47 according to the embodiment is provided along the entire periphery of each of the second fixing part 46 and the diaphragm 42. The escape hole may not necessarily be provided along the entire periphery but may be provided only along a portion of the periphery of each of the second fixing part 46 and the diaphragm 42.

The first valve housing 38 and the second valve housing 40 configured as described above are fixed and assembled together as follows. First, the double-faced tape constituting each of the first and second fixing parts 44 and 46 is affixed to a face of the second valve housing 40. Subsequently, the outer edge region of the diaphragm 42 is stuck to the back face of the second fixing part 46 to thereby fix the diaphragm 42 in place. Then, the adhesive constituting the third fixing part 58 is applied between the first fixing part 44 and the second fixing part 46. In that state, the first valve housing 38 is bonded to the back face of the first fixing part 44 and the back face of the third fixing part 58 to thereby fix the first valve housing 38 in place. At this time, any excess adhesive in the third fixing part 58 is allowed to flow out through the escape hole 47 so as to sit on top of the diaphragm 42. This helps to improve the precision of the fixing performed by using the adhesive. Further, the diaphragm 42 can be fixed to the second valve housing 40 before the first valve housing 38 is fixed to the second valve housing 40. This ensures that the diaphragm 42 can be fixed in place without being obstructed by the valve seat 50 of the first valve housing 38.

Figure 6A:
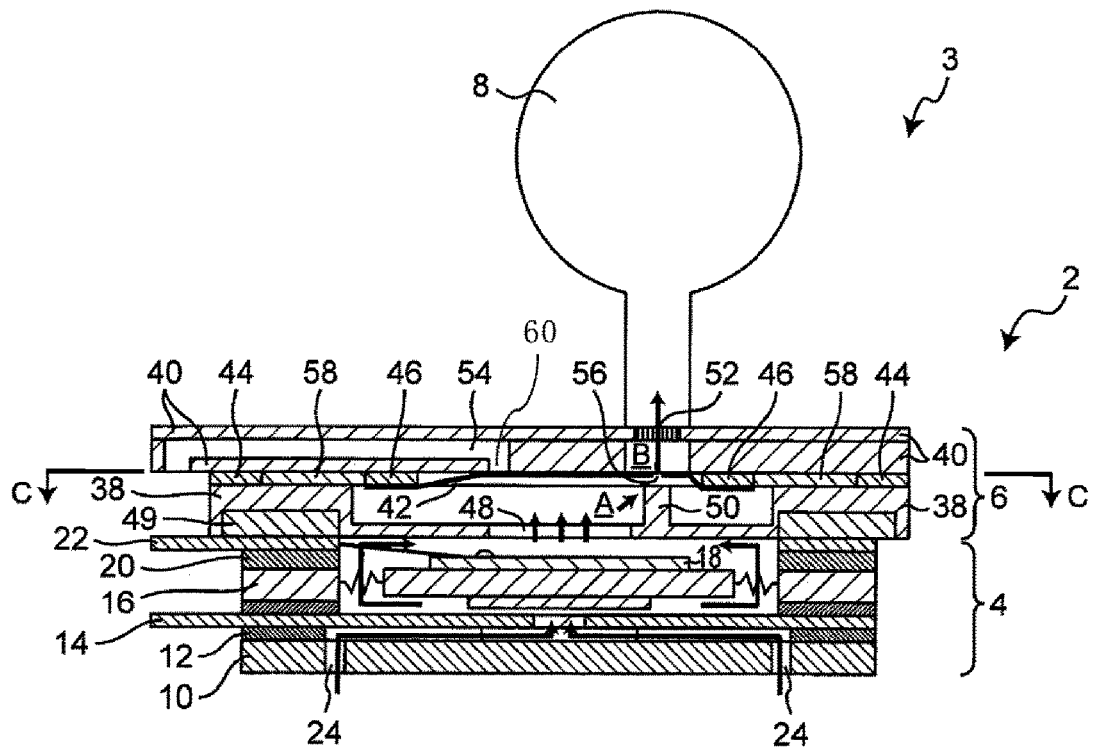
FIG. 6A is a longitudinal sectional view of the fluid control device for explaining its operation (communicating state, the second position).
Figure 6B:
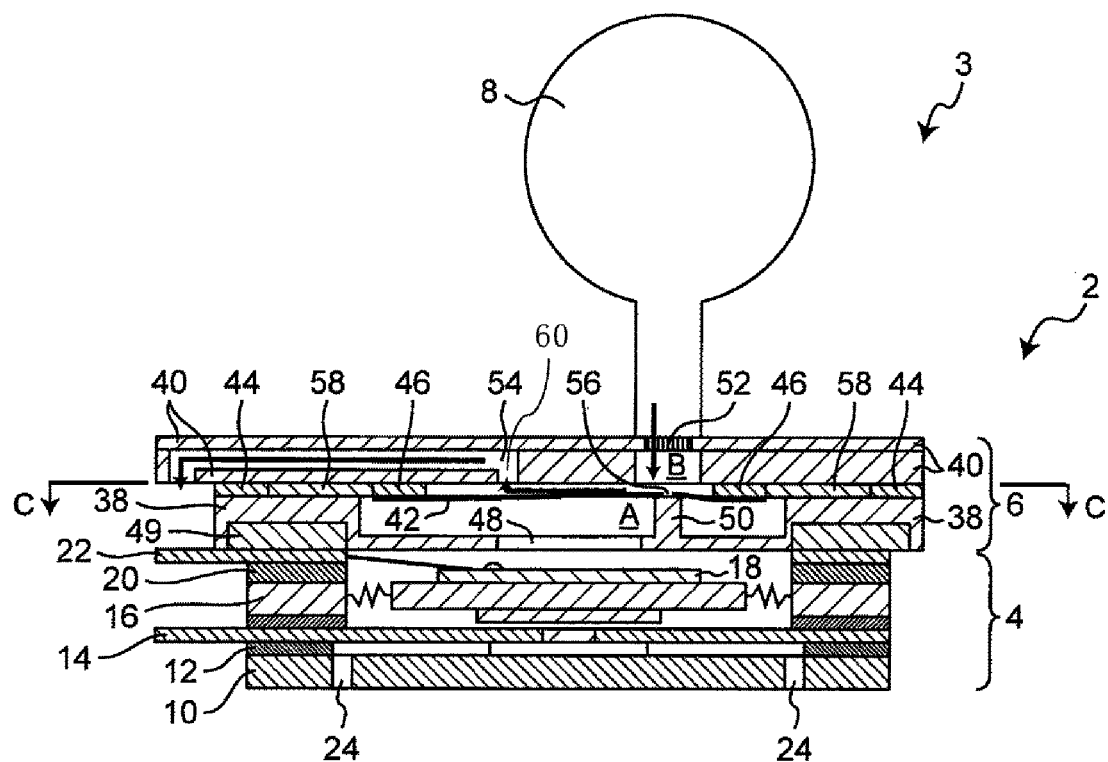
FIG. 6B is a longitudinal sectional view of the fluid control device for explaining its operation (non-communicating state, the first position).

With reference to FIGS. 6A and 6B, the following describes the operation of the sphygmomanometer 3 including the pump 4, the valve 6, and the cuff 8 mentioned above. FIGS. 6A and 6B are both longitudinal sectional views for explaining the operation of the sphygmomanometer 3.

When the pump 4 is put into operation from the non-operating state illustrated in FIG. 4, as described above, a fluid (air at atmospheric pressure) is sucked in through the suction openings 24, and pressurized fluid is generated in the pump 4. The pressurized fluid thus generated flows into the valve 6 through the inlet 48 of the first valve housing 38.

The incoming pressurized fluid causes the pressure in the upstream valve chamber A to rise to a value exceeding the pressure (atmospheric pressure) in the downstream valve chamber B. Thus, as illustrated in FIG. 6A, the central portion of the diaphragm 42 not fixed in place by the second fixing part 46 moves away from the first valve housing 38 toward the second valve housing 40. Thus, the portion of the diaphragm 42 corresponding to the communication opening 56 and its periphery moves away from the valve seat 50 of the first valve housing 38. As the diaphragm 42 moves in this way, the diaphragm 42 blocks an inlet 60 of the second discharge channel 54 of the second valve housing 40. At this time, the second discharge channel 54 and the first discharge channel 52 become non-communicating, and the diaphragm 42 forms a seal between the second discharge channel 54 and the first discharge channel 52.

As a result of the above-mentioned operation, the diaphragm 42 moves from a first position illustrated in FIG. 4 in which the diaphragm 42 blocks communication between the upstream valve chamber A and the downstream valve chamber B, to a second position illustrated in FIG. 6A in which the diaphragm 42 allows communication between the upstream valve chamber A and the downstream valve chamber B. In the second position illustrated in FIG. 6A, pressurized fluid is allowed to flow from the upstream valve chamber A to the downstream valve chamber B, and then sent to the cuff 8 through the first discharge channel 52. As the pump 4 continues to operate, the pressurized fluid is sequentially sent to the cuff 8, causing the cuff 8 to inflate and thus function as an air bag used for measuring blood pressure.

In the operating state illustrated in FIG. 6A, the surface of the diaphragm 42 is subjected mainly to a pressure exerted by pressurized fluid, and only a portion of the surface of the diaphragm 42, that is, the area corresponding to the inlet 60 of the second discharge channel 54 is subjected to atmospheric pressure. Hence, only a small portion of the diaphragm 42 is subjected to a large differential pressure, and the differential pressure across the diaphragm 42 as a whole is small.

When the blood pressure measurement is finished, the operation of the pump 4 is stopped. Upon stopping the operation of the pump 4, the supply of pressurized fluid by the pump 4 stops, and the pressure in the internal space of the pump 4 drops. This causes a pressure drop in each of the upstream and downstream valve chambers A and B of the valve 6. Thus, the pressure in the vicinity of the cuff 8 becomes higher than the pressure in each of the upstream and downstream valve chambers A and B. This causes the pressurized fluid stored in the cuff 8 to return to the downstream valve chamber B. Due to the flow of the pressurized fluid returning to the downstream valve chamber B, the central portion of the diaphragm 42 moves in a direction away from the second valve housing 40 and toward the first valve housing 38. As a result, as illustrated in FIG. 6B, the diaphragm 42 returns to its original first position, and the portion of the diaphragm 42 around the communication opening 56 makes contact with the valve seat 50 to form a seal. At the same time, the diaphragm 42 separates from the inlet 60 of the second discharge channel 54 to release the second discharge channel 54. At this time, the first discharge channel 52 and the second discharge channel 54 are placed in communication with each other.

In the state illustrated in FIG. 6B, the flow of fluid from the downstream valve chamber B to the upstream valve chamber A is blocked. Thus, pressurized fluid flowing into the downstream valve chamber B through the first discharge channel 52 is routed into the second discharge channel 54. At this time, the second discharge channel 54 communicates with the outside of the valve 6, and thus the pressurized fluid is exhausted to the atmosphere. In this way, the pressurized fluid can be rapidly exhausted after the operation of the pump 4 is stopped. Due to the rapid exhausting of the pressurized fluid, the pressure in the downstream valve chamber B becomes the same atmospheric pressure as the upstream valve chamber A.

In the non-operating state illustrated in FIG. 6B, only atmospheric pressure acts on the surface the diaphragm 42, resulting in a differential pressure of substantially zero.

With the fluid control device 2 according to the embodiment above, the diaphragm 42 is fixed inward of the first fixing part 44, and is not exposed to the outside of the first and second valve housings 38 and 40. If the diaphragm 42 is exposed to the outside of the first and second valve housings 38 and 40, the surface of the diaphragm 42 is subjected to a large differential pressure due to the pressurization state inside the valve 6 and the atmospheric pressure outside the valve 6. By contrast, the diaphragm 42 according to the embodiment is disposed inside the first valve housing 38 and the second valve housing 40. This reduces the differential pressure across the surface of the diaphragm 42. The reduced differential pressure helps to reduce degradation of and damage to the diaphragm 42 and consequently extend the life of the diaphragm 42.

Further, in a plan view, the diaphragm 42 is fixed inward of the first fixing part 44. This makes it possible to reduce the length of the diaphragm 42.

With the fluid control device 2 according to the embodiment, the second fixing part 46 fixes the diaphragm 42 to the second valve housing 40. This configuration makes it possible to fix the diaphragm 42 to the second valve housing 40 before the first valve housing 38 is fixed to the second valve housing 40. As a result, the diaphragm 42 can be fixed in place without being obstructed by the valve seat of the first valve housing 38, thus facilitating manufacture of the fluid control device 2.

With the fluid control device 2 according to the embodiment, the third fixing part 58 is provided in addition to the first fixing part 44 and the second fixing part 46. This configuration allows the first valve housing 38 and the second valve housing 40 to be fixed more firmly in place. This configuration also makes it possible to use a different material for each of the first fixing part 44, the second fixing part 46, and the third fixing part 58. For example, depending on the material of a component to be bonded, a material that allows for easy fixing of metal (e.g., epoxy-based material), or a material that allows for easy fixing of rubber (e.g., acrylic rubber-based material) can be used for each fixing part.

With the fluid control device 2 according to the embodiment, a double-faced tape is used as the first fixing part 44 and the second fixing part 46, and an adhesive is used as the third fixing part 58. Thus, a double-faced tape, which has no fluidity, is used as the first fixing part 44 that is the outermost fixing part. This facilitates positioning of the first fixing part 44. Further, unlike an adhesive, a double-faced tape is not susceptible to leak paths and thus can reliably seal the valve 6. Further, using an adhesive as the third fixing part 58 allows for increased fixing strength. Although the adhesive constituting the third fixing part 58 has high fluidity, the third fixing part 58 is held back by the first fixing part 44 and the second fixing part 46, and thus can be placed at a desired location.

With the fluid control device 2 according to the embodiment, a silicone adhesive is used as the third fixing part 58. Using such a general-purpose material helps to reduce the manufacturing cost of the fluid control device 2.

With the fluid control device 2 according to the embodiment, a step is provided between the first opposing face 38A and the second opposing face 38B to define the escape hole 47. This configuration makes it possible to provide a space that, if the third fixing part 58 has an excessive amount of adhesive, allows any excess adhesive in the third fixing part 58 to escape through the escape hole 47.

With the fluid control device 2 according to the embodiment, as illustrated in FIG. 6A, when in its second position, the diaphragm 42 makes contact with and blocks the inlet 60 of the second discharge channel 54 to provide a seal between the second discharge channel 54 and the first discharge channel 52. This configuration ensures that the diaphragm 42 can, when in its second position, seal between the second discharge channel 54 and the first discharge channel 52 with increased precision.

Although the present disclosure has been described above by way of the embodiment above, the present disclosure is not limited to the above embodiment. For example, in the foregoing description of the embodiment, the pump 4 is a piezoelectric pump including the piezoelectric body 18. However, this may not necessarily be the case. Other than a piezoelectric pump, any type of pump capable of generating pressurized fluid may be used.

In the foregoing description of the embodiment, the fluid control device 2 is used in the sphygmomanometer 3 including the cuff 8. However, this may not necessarily be the case.

The fluid control device 2 may be used for applications other than blood pressure measurement.

In the foregoing description of the embodiment, the diaphragm 42 is fixed to the second valve housing 40. However, this may not necessarily be the case. Alternatively, the diaphragm 42 may be fixed to the first valve housing 38. In other words, the diaphragm 42 may only need to be fixed to one of the first valve housing 38 and the second valve housing 40.

In the foregoing description of the embodiment, a double-faced tape is used as the first fixing part 44 and the second fixing part 46. However, this may not necessarily be the case. Alternatively, a material other than a double-faced tape may be used. Examples of such materials may include epoxy resin, structural acrylic resin, ester resin (polyester), and melanin resin. In this case, an adhesive with a lower fluidity than the adhesive constituting the third fixing part 58 may be used to thereby effectively hold back the adhesive constituting the third fixing part 58.

In the foregoing description of the embodiment, the third fixing part 58 is provided in addition to the first fixing part 44 and the second fixing part 46. However, this may not necessarily be the case. The third fixing part 58 may not be provided. If the third fixing part 58 is not provided, for example, the first fixing part 44 and the second fixing part 46 may be formed as the same double-faced tape.

In the foregoing description of the embodiment, a silicone adhesive is used as the third fixing part 58. However, this may not necessarily be the case. An adhesive other than a silicone adhesive may be used as the third fixing part 58. Examples of such adhesives may include a polysulfide resin adhesive and an acrylic rubber adhesive.

In the foregoing description of the embodiment, when in its second position, the diaphragm 42 makes contact with and blocks the inlet 60 of the second discharge channel 54 to thereby provide a seal between the second discharge channel 54 and the first discharge channel 52. However, this may not necessarily be the case. For example, the diaphragm 42 may make contact not with the inlet 60 of the second discharge channel 54 but with the wall surface of the downstream valve chamber B to thereby provide a seal between the second discharge channel and the first discharge channel. That is, in this case, the diaphragm 42 may, when in its second position, make contact with either the inlet 60 of the second discharge channel 54 or the wall surface of the downstream valve chamber B to thereby provide a seal between the second discharge channel 54 and the first discharge channel 52.

Although the present disclosure has been described in sufficient detail by way of its preferred embodiments with reference to the accompanying drawings, various modifications and alterations will be apparent to those skilled in the art. Such modifications and alterations are to be understood as falling within the scope of the present disclosure as defined by the appended claims without departing therefrom. Any changes in the combination or sequential order of elements in the embodiments can be accomplished without departing from the scope and spirit of the present disclosure.

The present disclosure is useful for a valve, and a fluid control device including a valve.

2 fluid control device
3 sphygmomanometer
4 pump
6 valve
8 cuff
10 cover
12 channel plate
14 thin top plate
16 spring plate
18 piezoelectric body
20 insulating plate
22 power feeding plate
24 suction opening
26 channel
28 opening
30 vibrating part
32 frame part
34 connecting part
36 terminal
38 first valve housing
40 second valve housing
42 diaphragm
44 first fixing part
46 second fixing part
47 escape hole
48 inlet
49 adhesive
50 valve seat
52 first discharge channel
54 second discharge channel
56 communication opening
58 third fixing part
60 inlet
A upstream valve chamber
B downstream valve chamber

The invention claimed is:

1. A valve comprising:
a first valve housing having an inlet for pressurized fluid, and a valve seat;
a second valve housing having a first discharge channel for pressurized fluid, and a second discharge channel for pressurized fluid, the second valve housing being stacked over the first valve housing;
a diaphragm disposed between the first valve housing and the second valve housing, the diaphragm having a communication opening;
a first fixing part fixing an outer edge region of the first valve housing, and an outer edge region of the second valve housing to each other; and
a second fixing part separate from and disposed inward of the first fixing part in a plan view to fix the diaphragm to one of the first valve housing and the second valve housing,
wherein the diaphragm defines an upstream valve chamber together with the first valve housing,
wherein the diaphragm defines a downstream valve chamber together with the second valve housing,
wherein the diaphragm is movable between
a first position in which a portion of the diaphragm around the communication opening is positioned in contact with the valve seat of the first valve housing to block communication between the upstream valve chamber and the downstream valve chamber, and
a second position in which the portion of the diaphragm around the communication hole is positioned away from the valve seat of the first valve housing to allow communication between the upstream valve chamber and the downstream valve chamber, and
wherein when in the second position, the diaphragm makes contact with an inlet of the second discharge channel or with a wall surface of the downstream valve chamber to seal between the second discharge channel and the first discharge channel, and when in the first position, the diaphragm allows communication between the first discharge channel and the second discharge channel.

2. The valve according to claim 1, wherein when in the second position, the diaphragm makes contact with and blocks the inlet of the second discharge channel to seal between the second discharge channel and the first discharge channel.

3. A fluid control device comprising:
the valve according to claim 1; and
a pump configured to send pressurized fluid to the inlet of the first valve housing of the valve.

4. The valve according to claim 1, the first fixing part and the second fixing part being coplanar.

5. The valve according to claim 1, the first fixing part circumscribing the second fixing part.

6. A valve comprising:
a first valve housing having an inlet for pressurized fluid, and a valve seat;
a second valve housing having a first discharge channel for pressurized fluid, and a second discharge channel for pressurized fluid, the second valve housing being stacked over the first valve housing;
a diaphragm disposed between the first valve housing and the second valve housing, the diaphragm having a communication opening;
a first fixing part fixing an outer edge region of the first valve housing, and an outer edge region of the second valve housing to each other; and
a second fixing part disposed inward of the first fixing part in a plan view to fix the diaphragm to one of the first valve housing and the second valve housing,
wherein the diaphragm defines an upstream valve chamber together with the first valve housing,
wherein the diaphragm defines a downstream valve chamber together with the second valve housing,
wherein the diaphragm is movable between
a first position in which a portion of the diaphragm around the communication opening is positioned in contact with the valve seat of the first valve housing to block communication between the upstream valve chamber and the downstream valve chamber, and
a second position in which the portion of the diaphragm around the communication hole is positioned away from the valve seat of the first valve housing to allow communication between the upstream valve chamber and the downstream valve chamber,
wherein when in the second position, the diaphragm makes contact with an inlet of the second discharge channel or with a wall surface of the downstream valve chamber to seal between the second discharge channel and the first discharge channel, and when in the first position, the diaphragm allows communication between the first discharge channel and the second discharge channel, and
wherein the second fixing part fixes the diaphragm to the second valve housing.

7. The valve according to claim 6, further comprising
a third fixing part disposed between the first fixing part and the second fixing part in a plan view to fix the first valve housing and the second valve housing to each other.

8. The valve according to claim 6,
wherein when in the second position, the diaphragm makes contact with and blocks the inlet of the second discharge channel to seal between the second discharge channel and the first discharge channel.

9. A fluid control device comprising:
the valve according to claim 6; and
a pump configured to send pressurized fluid to the inlet of the first valve housing of the valve.

10. A valve comprising:
a first valve housing having an inlet for pressurized fluid, and a valve seat;
a second valve housing having a first discharge channel for pressurized fluid, and a second discharge channel for pressurized fluid, the second valve housing being stacked over the first valve housing;
a diaphragm disposed between the first valve housing and the second valve housing, the diaphragm having a communication opening;
a first fixing part fixing an outer edge region of the first valve housing, and an outer edge region of the second valve housing to each other;
a second fixing part disposed inward of the first fixing part in a plan view to fix the diaphragm to one of the first valve housing and the second valve housing; and
a third fixing part disposed between the first fixing part and the second fixing part in a plan view to fix the first valve housing and the second valve housing to each other,
wherein the diaphragm defines an upstream valve chamber together with the first valve housing,
wherein the diaphragm defines a downstream valve chamber together with the second valve housing,
wherein the diaphragm is movable between
a first position in which a portion of the diaphragm around the communication opening is positioned in contact with the valve seat of the first valve housing to block communication between the upstream valve chamber and the downstream valve chamber, and
a second position in which the portion of the diaphragm around the communication hole is positioned away from the valve seat of the first valve housing to allow communication between the upstream valve chamber and the downstream valve chamber, and
wherein when in the second position, the diaphragm makes contact with an inlet of the second discharge channel or with a wall surface of the downstream valve chamber to seal between the second discharge channel and the first discharge channel, and when in the first position, the diaphragm allows communication between the first discharge channel and the second discharge channel.

11. The valve according to claim 10,
wherein the first fixing part and the second fixing part each comprise a double-faced tape, and the third fixing part comprises an adhesive.

12. The valve according to claim 11,
wherein the third fixing part comprises a silicone adhesive.

13. The valve according to claim 12,
wherein the first valve housing has
a first opposing face extending flush from an area where the first valve housing makes contact with the second valve housing in the first fixing part, to a point within an area where the first valve housing makes contact with the second valve housing in the third fixing part, and
a second opposing face recessed from an inner edge portion of the first opposing face and extending flush such that the second opposing face is spaced apart from the third fixing part and the diaphragm.

14. The valve according to claim 12,
wherein when in the second position, the diaphragm makes contact with and blocks the inlet of the second discharge channel to seal between the second discharge channel and the first discharge channel.

15. The valve according to claim 11,
wherein the first valve housing has
- a first opposing face extending flush from an area where the first valve housing makes contact with the second valve housing in the first fixing part, to a point within an area where the first valve housing makes contact with the second valve housing in the third fixing part, and
- a second opposing face recessed from an inner edge portion of the first opposing face and extending flush such that the second opposing face is spaced apart from the third fixing part and the diaphragm.

16. The valve according to claim 11,
wherein when in the second position, the diaphragm makes contact with and blocks the inlet of the second discharge channel to seal between the second discharge channel and the first discharge channel.

17. The valve according to claim 10,
wherein the first valve housing has
- a first opposing face extending flush from an area where the first valve housing makes contact with the second valve housing in the first fixing part, to a point within an area where the first valve housing makes contact with the second valve housing in the third fixing part, and
- a second opposing face recessed from an inner edge portion of the first opposing face and extending flush such that the second opposing face is spaced apart from the third fixing part and the diaphragm.

18. The valve according to claim 17,
wherein when in the second position, the diaphragm makes contact with and blocks the inlet of the second discharge channel to seal between the second discharge channel and the first discharge channel.

19. The valve according to claim 10,
wherein when in the second position, the diaphragm makes contact with and blocks the inlet of the second discharge channel to seal between the second discharge channel and the first discharge channel.

20. A fluid control device comprising:
the valve according to claim 10; and
a pump configured to send pressurized fluid to the inlet of the first valve housing of the valve.

* * * * *